US008604189B2

(12) United States Patent
Gurjar et al.

(10) Patent No.: US 8,604,189 B2
(45) Date of Patent: Dec. 10, 2013

(54) PROCESS FOR THE PREPARATION OF EFAVIRENZ

(75) Inventors: Mukund Keshav Gurjar, Pune (IN); Abdulrakheeb Abdulsubhan Deshmukh, Pune (IN); Sanjay Shankar Deshmukh, Pune (IN); Satish Ramanial Mehta, Pune (IN)

(73) Assignee: Emcure Pharmaceuticals Limited, Pune (IN)

( * ) Notice: Subject to any disclaimer, the term of this patent is extended or adjusted under 35 U.S.C. 154(b) by 353 days.

(21) Appl. No.: 12/995,209

(22) PCT Filed: May 27, 2009

(86) PCT No.: PCT/IN2009/000307
§ 371 (c)(1),
(2), (4) Date: Nov. 30, 2010

(87) PCT Pub. No.: WO2010/032259
PCT Pub. Date: Mar. 25, 2010

(65) Prior Publication Data
US 2011/0077397 A1      Mar. 31, 2011

(30) Foreign Application Priority Data
May 30, 2008   (IN) .................. 1155/MUM/2008

(51) Int. Cl.
*C07D 265/18*    (2006.01)
(52) U.S. Cl.
USPC .......................................... 544/92; 564/442
(58) Field of Classification Search
USPC .................................................... 544/92
See application file for complete search history.

(56) References Cited

U.S. PATENT DOCUMENTS

| 5,519,021 A | 5/1996 | Young et al. |
| 5,633,405 A | 5/1997 | Thompson et al. |
| 5,932,726 A | 8/1999 | Pierce et al. |
| 6,015,926 A * | 1/2000 | Chen et al. ............... 564/442 |
| 6,114,569 A | 9/2000 | Frey et al. |
| 6,147,210 A | 11/2000 | Pierce et al. |
| 2005/0256103 A1 | 11/2005 | Suzuki et al. |

FOREIGN PATENT DOCUMENTS

WO    WO 2009/133538 A1    11/2009

OTHER PUBLICATIONS

Heiner Eckert et al. Angewandte Chemie International Edition, vol. 26, No. 9, 1987, pp. 894-895.*
Pierce et al., "Practical Asymmetric Synthesis of Efavirenz (DMP 266), an HIV-1 Reverse Transcriptase Inhibitor," Journal of Organic Chemistry, vol. 63 No. 23, 1998, pp. 8536-8543.
Thompson et al., Use of an Ephedrine Alkoxide to Mediate Enantioselective Addition of an Acetylide to a Prochiral Ketone: Asymmetric Synthesis of the Reverse Transcriptase Inhibitor L-743,726, Tetrahedron Letters, vol. 36, No. 49, 1995, pp. 8937-8940.
Pedersen et al., "The Flourishing Syntheses of Non-Nucleoside Reverse Transcriptase Inhibitors," Synthesis 2000, No. 4, pp. 479-495.
Radesca et al., "Synthesis of HIV-1 Reverse Transcriptase Inhibitor DMP 266," Synthetic Communications, vol. 27, No. 24, 1997, pp. 4373-4384.
Furniss et al., Vogel's Textbook of Practical Organic Chemistry, 5th Edition, pp. 406-407, (1989).
Heiner Eckert et al., "Triphosgene, a Crystalline Phosgene Substitute", Angewandte Chemie. International Edition, Wiley Vch Verlag, Weinheim, vol. 26, No. 9, Jan. 1, 1987, p. 894-895, XP002083416, ISSN: 1433-7851.
Cotarca L. et al., "Bis(trichloromethyl) Carbonate in Organic Synthesis", Synthesis, Georg Thieme Verlag, Stuttgart, DE, Jan. 1, 1996, pp. 553-576, XP002090854, ISSN: 0039-7881.
PCT/IN2009/000307 International Preliminary Report on Patentability and Written Opinion of the International Searching Authority, issued Sep. 3, 2010, 13 pages.

* cited by examiner

*Primary Examiner* — Kahsay Habte
(74) *Attorney, Agent, or Firm* — Fulbright & Jaworski, LLP; Erik G. Swenson

(57) ABSTRACT

A simple, cost-effective process for preparation of efavirenz of formula (I) comprising reacting a solution of 5-chloro-α-(cyclopropylethynyl)-2-amino-α-trifluoromethyl) benzene methanol of formula (II) in an organic solvent with triphosgene in the presence of an inorganic base at a temperature range −5° C. to 25° C., adding water and isolating compound of formula (I).

4 Claims, No Drawings

PROCESS FOR THE PREPARATION OF EFAVIRENZ

CROSS-REFERENCE TO RELATED APPLICATIONS

This application is a Section 371 National Stage Application of International No. PCT/IN2009/000307, filed May 27, 2009 and published as WO 2010/032259 A2 on Mar. 25, 2010, which claims priority from the India Application 1155/MUM/2008, filed May 30, 2008, the contents of which are incorporated herein in their entirety for all purposes.

FIELD OF THE INVENTION

The invention relates to a novel and simple, cost-effective process for the preparation of a reverse transcriptase inhibitor.

BACKGROUND OF THE INVENTION

Acquired Immunodeficiency Syndrome (AIDS) is a fatal disease of the immune system transmitted through blood especially by sexual contact or contaminated needles and is presumed to be caused by the HIV virus, which is an RNA genetically unique retrovirus, having a gene not found to date in other retroviruses.

One of the many drugs found to be active against HIV virus is efavirenz of formula (I), chemically known as (−)-6-Chloro-4-cyclopropyl-ethynyl-4-trifluoromethyl-1,4-dihydro-2H-3.1-benzoxazin-2-one. Efavirenz marketed as Sustiva is clinically active specifically against human immunodeficiency virus type 1 (HIV-1) and is a non-nucleoside, reverse transcriptase inhibitor. The activity of Efavirenz is mediated predominantly by non-competitive inhibition of HIV-1 RT without affecting HIV-2 RT and human cellular DNA polymerases alpha, beta, gamma and delta.

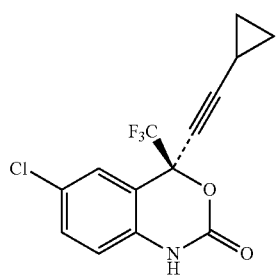

(I)

U.S. Pat. No. 5,519,021 (assigned to Merck) discloses a method in which efavirenz (I) is obtained by reaction of 2-(2-amino-5-chlorophenyl)-4-cyclopropyl-1,1,1-trifluoro-3-butyn-2-ol of formula (II) with a large excess of carbonyl diimidazole of formula (III) for obtaining the oxazinone ring.

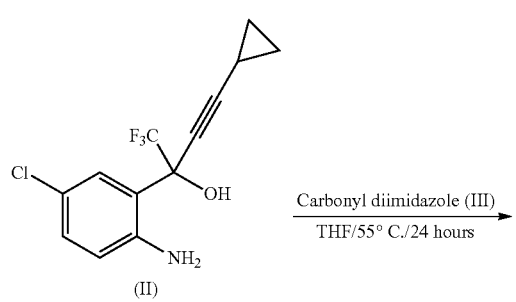

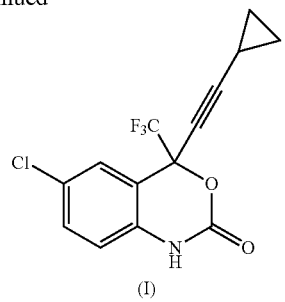

(I)

The reaction utilizes dry tetrahydrofuran as solvent and which has a tendency to develop peroxides during storage. In order to obtain dry tetrahydrofuran free of peroxides, purification and drying agents are required, and such process of purification and drying adds on to the cost. As reported in the widely accepted literature, Textbook of Practical Organic Chemistry—Vogel; $5^{th}$ Edition, page 406-407 discloses use of solid potassium hydroxide followed by refluxing over calcium hydride or lithium aluminium hydride for drying tetrahydrofuran, which is not advisable on a commercial scale due to the fire catching tendency and explosive nature of the metallic hydrides. Also, the related note draws attention towards the hazards of drying with respect to peroxides during purification. Further, the volume of tetrahydrofuran utilized is also about 16 times of starting material, which is quite exorbitant for commercial use.

The reaction is carried out at 55° C. and takes about 24 hours for completion. Also, the work up of the reaction involving distillation of tetrahydrofuran is quite risky and dangerous due to the potential of tetrahydrofuran to develop peroxides. The residue obtained after concentration is redissolved in ethyl acetate and partitioned with water followed by re-extraction with ethyl acetate. The process also has an elaborate work up method requiring aqueous washings with dilute acid, alkaline solution and brine followed by separation of organic layer, drying over a drying agent and subsequent distillations, which consumes lot of time and utility. Moreover during such washings, there is a potential danger for formation of emulsion. This lowers the yield as in the case of U.S. Pat. No. 5,519,021 to about 85%, thereby making the process unsuitable for commercial purpose.

Therefore, U.S. Pat. No. 5,519,021 suffers from various shortcomings such as:

1) Risk of using tetrahydrofuran, which is known to have an explosive nature due to its tendency to develop peroxides on storage,
2) Requirement of stringent anhydrous conditions as dry tetrahydrofuran is employed as solvent for the reaction,
3) Large volume of tetrahydrofuran is required,
4) Long reaction time reduces the efficiency of the reaction and also increases the reactor occupancy,
5) Repeated washings with aqueous solvent such as dilute acid, alkaline solution and brine increases the load on the effluent treatment plant,
6) Tendency to form emulsion during alkaline work up reduces the yield.

U.S. Pat. No. 5,633,405 (assigned to Merck) discloses another process for obtaining an efavirenz derivative of formula (VI) by reaction of the amino alcohol of formula (IV) with phosgene utilizing a mixture of toluene and tetrahydrofuran as solvent and triethyl amine as a base. The use of tetrahydrofuran as already mentioned requires an additional step of purification for removal of peroxides.

Product isolation involves quenching with cold water, followed by extraction with yet another solvent like ethyl acetate. Based on the example, demulsification is carried out with saturated brine solution. Breaking of an emulsion generally takes long time and this affects the time cycle, reactor occupancy etc. Further washings of the organic layer are carried out with citric acid solution followed by brine solution. The organic layer thus obtained is dried over sodium sulphate and concentrated to give brown oil, which is then recrystallized from a 5:1 mixture of hexane:ethyl acetate to give the compound of formula (VI) in 85% yield.

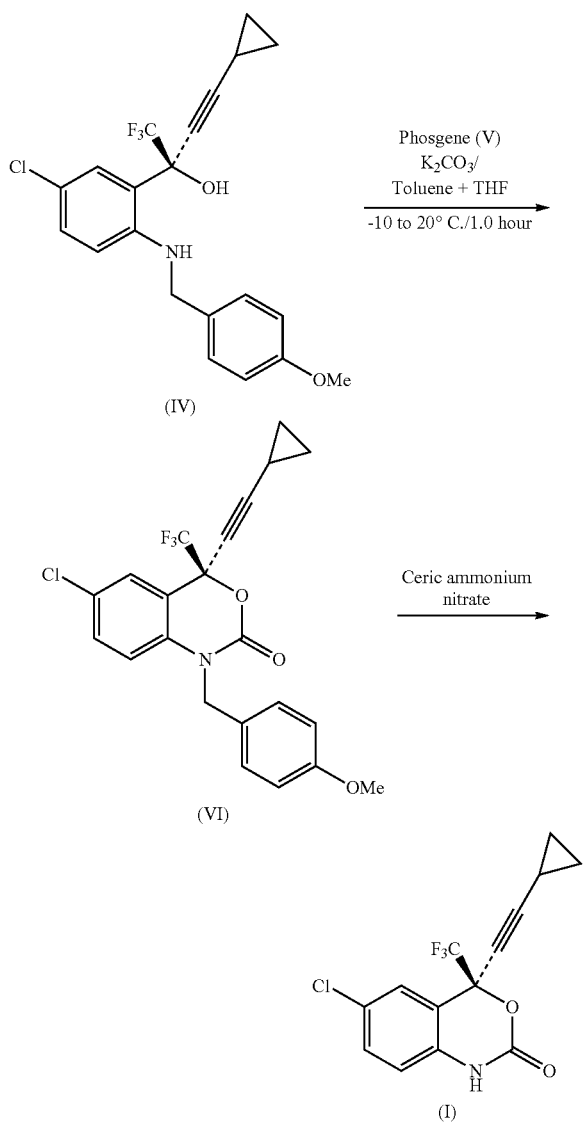

There is an additional step of deprotection of the nitrogen atom in the oxazinone ring of the compound of formula (VI) with a reagent like ceric ammonium nitrate to give efavirenz, which was isolated by column chromatography.

The process has the following disadvantages:

1) Reaction is carried out with a binary solvent mixture of toluene and tetrahydrofuran. Further, a third solvent like ethyl acetate is required for extraction to give the crude product. Also, a fourth solvent like hexane in combination with ethyl acetate is employed for purification of the product of formula (VI). Utilization of four different solvents leads to manifold increase in cost, raises the inventory of solvents and further also increases the load on the effluent due to the use of a water-miscible solvent like tetrahydrofuran.

2) The specification itself acknowledges that emulsification is an inherent part of the process. Isolation of any product from an emulsion is quite tedious and cumbersome on an industrial scale, leading to loss in yield.

3) The product obtained after such a laborious work-up requires purification by recrystallization.

4) Utilization of ceric ammonium nitrate in the final deprotection step to give efavirenz (I) generates an enormous load on effluent treatment as it is quite difficult to remove the heavy metal on a commercial scale. In short, the whole process is quite long, thereby reducing the overall efficiency of the process.

This process has also been disclosed in Journal of Organic Chemistry 1998, 63, 8536-8543 and Tetrahedron Letters 1995, 36, 8937-8940.

U.S. Pat. No. 5,932,726 (assigned to DuPont) discloses a process for the preparation of efavirenz of formula (I) by reaction of the efavirenz intermediate (II) with phosgene in a solvent such as heptane, toluene and tetrahydrofuran or mixtures thereof. The preferred solvent is a mixture of heptane and tetrahydrofuran. During the reaction, a third solvent like methanol is added. After the reaction heptane is added and the mixture partially concentrated. A mixture of heptane and tetrahydrofuran is added and the resulting mixture washed with aqueous sodium bicarbonate solution followed by water. The mixture was warmed to 50° C. and diluted with heptane to obtain the product.

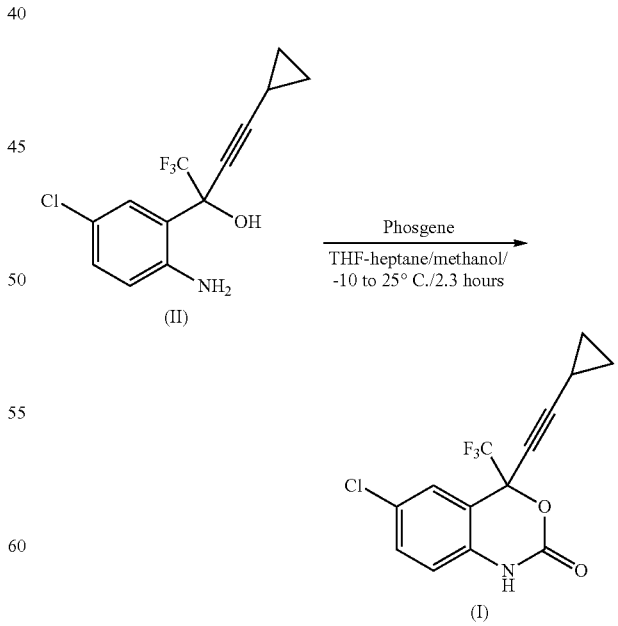

The drawbacks of the process are:
1) Process requires three solvents, namely heptane, tetrahydrofuran and methanol, Out of these 3 solvents, tetrahydrofuran (65° C.) and methanol (65° C.), have identical boiling points, therefore recovery of these solvents in a pure form is quite difficult. Both these solvents are water-soluble; hence recovery of these solvents based on their water solubility also is not possible, 2) The total volume of the solvents required for the reaction and before isolation is about 12 times the batch size. Isolation of the product requires an additional 9.0 times volume of a mixture of heptane and tetrahydrofuran. Therefore, the total volume required is about 21 times the batch size, which is quite high for reactions to be carried out on a large scale, leading to considerable cost escalation.

3) work-up involves distillation of tetrahydrofuran, which is very dangerous due to its explosive nature associated with peroxide formation during storage, 4) work up involves washing with dilute alkali solution wherein there is a tendency for emulsification, which is quiet tedious to remove on a commercial scale. Emulsification reduces the yield and demulsification consumes lot of time and energy on a large scale, Therefore, the process disclosed in U.S. Pat. No. 5,932,726 is quite costly and not feasible due to the large amount of solvents, and is also lengthy, laborious, cumbersome for industrial scale.

Synthesis 2000, 4, 479-495 and Journal of Organic Chemistry 1998, 63(23) 8536-8543 also discloses a similar process for the preparation of the benzoxazinone ring for the preparation of efavirenz of formula (I).

U.S. Pat. No. 6,147,210 (assigned to DuPont Pharmaceuticals) discloses a process in which the desired benzoxazinone ring was obtained comprising reaction of compound of formula (VII) in toluene/hexane mixture utilizing n-butyl lithium as base. The reaction was refluxed for 4 hours for completion of reaction. The product was isolated by quenching with a mixture of 5% acetic acid and t-butyl methyl ether. The organic layer was separated, washed twice with sodium chloride solution and concentrated to get a residue from which the product was isolated by addition of heptane.

This process has the following drawbacks:

1) The reaction requires about 5.5 times of a solvent mixture of toluene and acetonitrile followed by 5 times volume the batch size each of 5% acetic acid solution and methyl t-butyl ether. Also, an additional 5 times of a third solvent like heptane is added during isolation of the product. Thus, the total volume of solvent required is about 20 times the batch size, which reduces the batch size, increases the time cycle for each batch run and reduces the efficiency of the process.

2) Utilization of four solvents such as toluene, hexane, methyl tert-butyl ether and heptane increases the inventory of solvents. Further, the use of methyl tert-butyl ether as a solvent finds limited use due to environmental and health concerns as it easily pollutes ground water. Successive washings with sodium chloride solution during isolation of compound of formula (I) suggests that there is a distinct possibility of emulsion formation during work up. All these shortcomings dissuade the use of the above disclosed process for preparation of efavirenz on an industrial scale.

Synthetic Communications 27(24), 4373-4384 (1997) also reports a similar process.

U.S. Pat. No. 6,015,926 (assigned to Merck & Co) discloses a process for the preparation of efavirenz by reaction of amino alcohol of formula (II) with phosgene utilizing methyl tert-butyl ether or toluene as solvent and aqueous potassium bicarbonate solution. After the reaction, the organic layer is separated and after brine washing the organic layer is concentrated. Efavirenz of formula (I) is isolated after the addition of ethanol or isopropanol to the residue. The crude efavirenz thus obtained is recrystallized from a mixture of isopropanol and water.

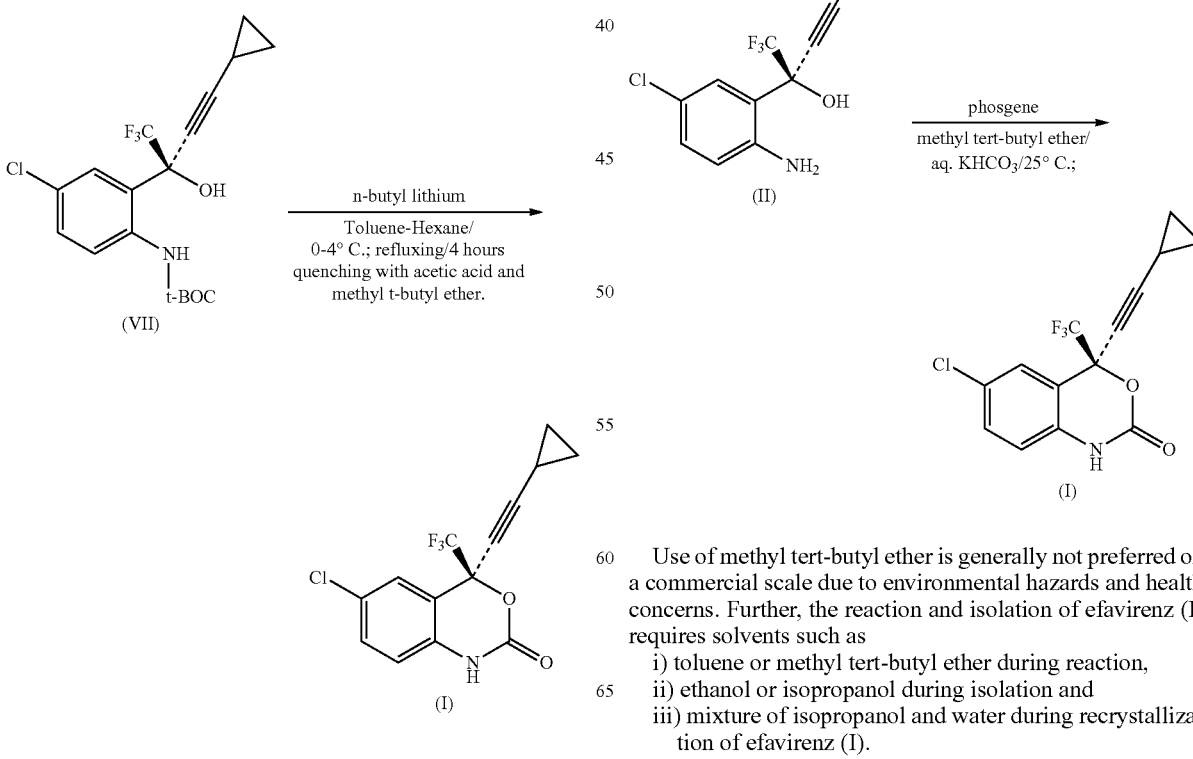

Use of methyl tert-butyl ether is generally not preferred on a commercial scale due to environmental hazards and health concerns. Further, the reaction and isolation of efavirenz (I) requires solvents such as
i) toluene or methyl tert-butyl ether during reaction,
ii) ethanol or isopropanol during isolation and
iii) mixture of isopropanol and water during recrystallization of efavirenz (I).

The requirement of multiple solvents increases the inventory and increase the process cost considerably.

U.S. Pat. No. 6,114,569 (assigned to Merck) discloses a process in which the benzoxazinone ring is formed by reaction of the carbamate derivative of an efavirenz intermediate of formula (VIII) in the presence of an aqueous solution of a base utilizing a solvent from the group selected from methyl t-butyl ether, toluene, tetrahydrofuran, acetonitrile, dimethyl acetamide, N-methylpyrrolidinone or mixtures thereof.

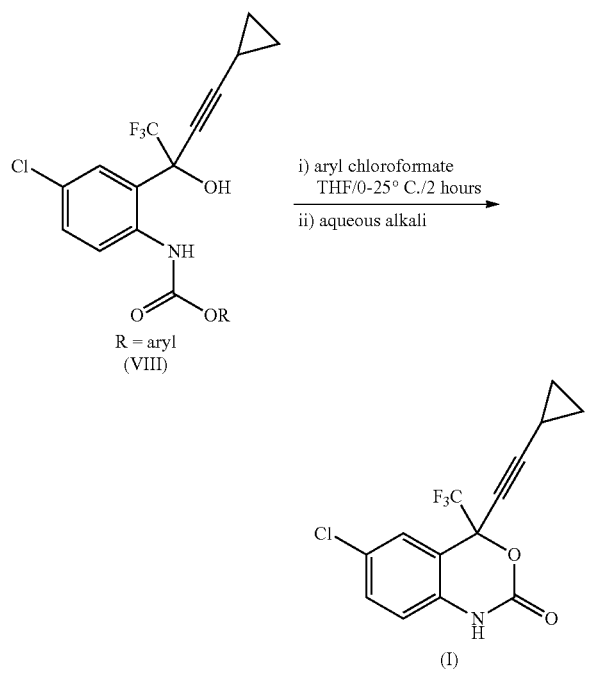

The reaction utilizes a high amount of solvent like tetrahydrofuran, up to 14 times the batch size for the reaction. After the reaction the mixture is quenched with an aqueous solution of a base (21 times), followed by addition of a second solvent like methyl tert-butyl ether (14 times). After the alkaline treatment, the organic layer was concentrated and the residue diluted with ethanol or isopropanol for isolation of the impure product of formula (I), which is then recrystallized from a high dilution (about 110 times) of an aqueous solution of isopropanol or ethanol.

This process although not utilizing phosgene for the preparation of the benzoxazinone ring has the following disadvantages:
 i) requires a solvent dilution of up to 14 times of the batch size during the reaction. Quenching is done with an additional 21 times batch size of an aqueous solution of an inorganic base. A second solvent such as methyl tert-butyl ether is added up to 14 times dilution. This raises the total volume to about 50 times, which is highly exorbitant on a commercial scale. Such high volumes drastically reduces the batch size,
 ii) Distillation of such high volume of solvent during isolation increases the time cycle for each batch run, consumes enormous amount of time, energy such that the efficiency of the process gets phenomenally reduced,
 iii) The compound of formula (I) thus isolated with enormously high dilution of solvent requires an additional recrystallization thus introducing an additional step of purification and also raises the cost tremendously.

Based on the foregoing, it is evident that prior art has the following drawbacks:
 1) Requires anhydrous reaction condition. Further, utilization of solvents like tetrahydrofuran, which are prone to develop peroxides on storage, requires solvent purification for removing the peroxides.
 2) Requires high dilution of solvents, which reduces the batch size, increases the distillation time, eventually increasing the time cycle for each run, thereby reducing the efficiency of the process.
 3) Utilization of multiple solvents for obtaining compound of formula (I) increases the solvent inventory reduces the possibility of obtaining a pure solvent for reuse when boiling points are close. Use of multiple solvents also increases the process cost considerably.
 4) Emulsion formation during work up significantly reduces the yield or requires enormous time for de-emulsification.
 5) Efavirenz of formula (I) isolated after the cyclization requires an additional step of purification for obtaining the desired form of the product.
 6) Utilization of a reagent like ceric ammonium nitrate for deprotection of the nitrogen atom in the oxazinone ring drastically increases the load on the effluent treatment due to heavy metal contamination.

OBJECT OF THE INVENTION

An object of the invention is to provide a simple, efficient and cost-effective process for the preparation of efavirenz of formula (I) without the utilization of multiple organic solvents.

Another object of the invention is to provide efavirenz of formula (I) having pharmaceutically acceptable purity and with quantitative yield without an additional step of purification.

Yet another object of the invention is to provide efavirenz of formula (I) by reducing the solvent volume, processing time for each batch cycle and utilizing a simple work up procedure for isolation of efavirenz of formula (I).

SUMMARY OF THE INVENTION

One aspect of the invention relates to a process for preparing efavirenz of formula (I) comprising reaction of a compound of formula (II) with triphosgene in an organic solvent, in the presence of a base, adding water and isolating compound of formula (I).

Another aspect of the invention relates to a process for preparing efavirenz of formula (I) comprising reaction of a compound of formula (II) with triphosgene in an organic solvent, in the presence of an aqueous solution of an inorganic base, neutralizing the reaction mixture and adding water to isolate compound of formula (I).

DETAILED DESCRIPTION OF THE INVENTION

The present inventors after considering the deficiencies of prior art processes have developed a simple cost-effective process, which has the following features:
 1) Use of a single organic solvent for cyclization of the compound of formula (II) to give a compound of formula (I),
 2) Absence of anhydrous or other stringent conditions like low temperature for completion of reaction and isolation of product, 3) Utilization of optimal amount of solvent during the reaction,
4) Does not require a reagent like ceric ammonium nitrate for obtaining efavirenz of formula (I), thereby reducing the load considerably on the effluent,
5) Obviates the necessity for having an additional step of purification after isolation of compound of formula (I) from the reaction,
6) Absence of any extraction step or possibility of emulsion formation during isolation.

The present invention relates to a novel process for the preparation of efavirenz of formula (I) by a process comprising reaction of 5-chloro-α-(cyclopropyl ethynyl)-2-amino-α-(trifluoromethyl)benzenemethanol of formula (II) with triphosgene in an organic solvent and in the presence of a base. After completion of the reaction, the reaction was neutralized with an aqueous alkali carbonate or bicarbonate solution if required. Water was then added to the reaction mixture and the product separating out was filtered and dried. The product of formula (I) was obtained in quantitative yield with purity conforming to pharmacopeial specification. The product thus isolated did not require any further purification for preparing the desired form of efavirenz (I).

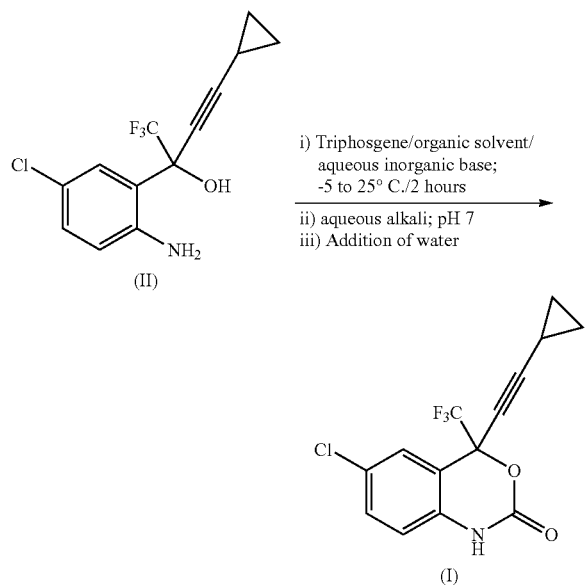

In a specific embodiment, 5-chloro-α-(cyclopropylethynyl)-2-amino-α-(trifluoromethyl) benzene methanol of formula (II) was added to an organic solvent.

The organic solvent was selected from the group comprising of ethers, nitriles, ketones, etc.

The organic solvent was selected from the group comprising of acetonitrile, propionitrile, butyronitrile, acetone, ethyl methyl ketone, THF and 1,2-dimethoxy ethane.

The organic solvent was preferably acetonitrile, acetone or 1,2-dimethoxy ethane.

The solvent added was between 1.0 volume and 3.0 volumes per gram of compound of formula (II).

Triphosgene of formula (V) dissolved in the same organic solvent was added gradually to the mixture containing compound of formula (II). This step was carried out at a temperature ranging from −5 to +25° C. Triphosgene as compared to phosgene gas was a crystalline solid and was very easy to handle on an industrial scale.

The base used was inorganic base and was selected from carbonates or bicarbonates of alkali or alkaline earth metal preferably, the carbonates or bicarbonates of alkali or alkaline earth metal particularly, sodium carbonate, potassium carbonate, sodium bicarbonate or potassium bicarbonate preferably sodium bicarbonate.

After completion of reaction in the same temperature range, the mixture was neutralized with an aqueous solution of an inorganic base. The inorganic base was selected from sodium carbonate, potassium carbonate, sodium bicarbonate or potassium bicarbonate.

Water was then added to the reaction mixture. The compound of formula (I) separating out was filtered, washed with water and dried.

Efavirenz of formula (I) was isolated in quantitative yield and was found to conform to pharmacopeial specification.

Efavirenz of formula (I) thus isolated, did not require any further recrystallizations or purification for obtaining the desired purity of Efavirenz of formula (I).

Efavirenz of formula (I) had X-ray diffraction (2θ) values and Differential Scanning Calorimetry data conforming to Form I of Efavirenz of formula (I).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

EXAMPLES

Example 1

(S)-5-Chloro-α-(cyclopropylethynyl)-2-amino-α-(trifluoromethyl) benzene methanol (100 gms; 0.345 moles) was added to acetonitrile (100 ml) in a 1000 ml flask, under continuous purging of nitrogen. Sodium bicarbonate (42.30 gms) dissolved in water (200 ml) was added to the flask at 25 to 30° C. and the mixture was cooled to −10° C. Triphosgene was dissolved in acetonitrile (50 gms; 0.168 moles in 200 ml of acetonitrile) was added to the reaction mixture between −10 and −5° C. The reaction mixture was stirred for 1 hour at −10 to −5° C. and was further stirred at 20-25° C. till completion of reaction as monitored by HPLC. The reaction mixture was optionally neutralized with dilute sodium carbonate solution. Water (150 ml) was gradually added to the reaction mixture at room temperature. The mixture was cooled to 10° C. to 15° C. and filtered. The wet cake was washed with DM water (400 ml) and dried under vacuum.

Yield: 106 gms.
% Yield: 97.25.
Purity: 99.72%.

Example 2

(S)-5-Chloro-α-(cyclopropylethynyl)-2-amino-α-(trifluoromethyl) benzene methanol (10 gms; 0.034 moles) was added to acetone (10 ml) in a 250 ml flask, with nitrogen purging. Sodium bicarbonate (4.3 gms; 0.05 moles) dissolved in water (20 ml) was added to the flask at 25 to 30° C. and the mixture was cooled to −10° C. Triphosgene dissolved in acetone (5 gms; 0.016 moles in 20 ml of acetone) and was added to the reaction mixture between −10 and −5° C. The reaction mixture was stirred for 1 hour at −10 to −5° C. and further, stirred at 20-25° C. till completion of reaction as monitored by HPLC. The reaction mixture was neutralized with sodium bicarbonate solution. Reaction mixture was filtered through 0.2 micron filter and was washed with 5 ml Acetone. Water (80 ml) was then gradually added to the reaction mixture at room temperature. The mixture was cooled to 10° C. to 15° C., and the product of formula (I) was filtered. The wet cake was washed with DM water (40 ml) and dried under vacuum.

Yield: 10.5 gms.
% Yield: 1.05% (w/w)
Purity: 99.84° A).

Example 3

(S)-5-Chloro-α-(cyclopropylethynyl)-2-amino-α-(trifluoromethyl) benzene methanol (5 gms; 0.017 moles) was added to tetrahydrofuran (5 ml) in a 250 ml flask, under continuous purging of nitrogen. Sodium bicarbonate (2.11 gms; 0.025 moles) dissolved in water (10 ml) was added to the flask at 25 to 30° C. and the mixture was cooled to −10° C. Triphosgene was dissolved in tetrahydrofuran (2.5 gms; 0.008 moles in 10 ml of Tetrahydrofuran) and added to the reaction mixture between −10 and −5° C. The reaction mixture was stirred for 1 hour at −10 to −5° C. and further, stirred at 20-25° C. till completion of reaction as monitored by HPLC. The reaction mixture was neutralized with dilute sodium bicarbonate solution. Reaction mixture was filtered through 0.2 micron filter and was washed with 2.5 ml tetrahydrofuran. Water (65 ml) was gradually added to the reaction mixture at room temperature. The mixture was cooled to 0° C. to 5° C., and filtered. The wet cake was washed with DM water (40 ml) and dried under vacuum.

Yield: 5.1 gms.
% Yield: 1.02% (w/w).
Purity: 99.67%.

Example 4

(S)-5-Chloro-α-(cyclopropylethynyl)-2-amino-α-(trifluoromethyl) benzene methanol (10 gms; 0.034 moles) was added to 1,2-Dimethoxy ethane (10 ml) in a 250 ml flask, under continuous purging of nitrogen. Sodium bicarbonate (3.6 gms; 0.042 moles) dissolved in water (20 ml) was added to the flask at 25 to 30° C. and the mixture cooled to −10° C. Triphosgene dissolved in 1,2-dimethoxy ethane (5 gms; 0.016 moles in 20 ml of 1,2-dimethoxy ethane) and added to the reaction mixture between −10 and −5° C. The reaction mixture was stirred for 1 hour at −10 to −5° C. and further stirred at 20-25° C. till completion of reaction as monitored by HPLC. The reaction mixture was neutralized with sodium carbonate solution (3 gms in 15 ml DM water). Reaction mixture was filtered through 0.2 micron filter and washed with 1,2-Dimethoxy ethane (5 ml). Water (80 ml) was gradually added to the reaction mixture at room temperature. The mixture was cooled to 10° C. to 15° C., and filtered. The wet cake was washed with DM water (40 ml) and dried under vacuum.

Yield: 9.9 gms.
% Yield: 99.00% (w/w).
Purity: 99.08%.

Example 5

(S)-5-Chloro-α-(cyclopropylethynyl)-2-amino-α-(trifluoromethyl) benzene methanol (10 gms; 0.034 moles) was added to propionitrile (10 ml) in a 250 ml flask, under continuous purging of nitrogen. Sodium bicarbonate (3.62 gms; 0.043 moles) dissolved in water (20 ml) was added to the flask at 25 to 30° C. and the mixture cooled to −10° C. Triphosgene was dissolved in acetone (5 gms; 0.016 moles in 20 ml of acetone) and added to the reaction mixture between −10 and −5° C. The reaction mixture was stirred for 1 hour at −10 to −5° C. and further stirred at 20-25° C. till completion of reaction as monitored by HPLC. Reaction mixture was filtered through 0.2 micron filter and washed with acetone (5 mL) followed by gradual addition of water (80 ml) to the reaction mixture at room temperature. The mixture was cooled to 10° C. to 15° C., and the product filtered. The wet cake was washed with DM water (40 ml) and dried under vacuum.

Yield: 10.0 gms.
% Yield: 1.0% (w/w).
Purity: 99.66%.

Example 6

(S)-5-Chloro-α-(cyclopropylethynyl)-2-amino-α-(trifluoromethyl) benzene methanol (10 gms; 0.034 moles) was added to butyronitrile (10 ml) in a 250 ml flask, under continuous purging of nitrogen. Sodium bicarbonate (3.44 gms; 0.05 moles) dissolved in water (20 ml) was added to the flask at 25 to 30° C. and the mixture cooled to −10° C. Triphosgene was dissolved in butyronitrile (5 gms; 0.016 moles in 20 ml of butyronitrile) and added to the reaction mixture between −10 and −5° C. The reaction mixture was stirred for 1 hour at −10 to −5° C. and further stirred at 20-25° C. till completion of reaction as monitored by HPLC. Reaction mixture was filtered through 0.2 micron filter and wash with 5 ml butyronitrile. Water (80 ml) was gradually added to the reaction mixture at room temperature. The mixture was cooled to 0° C. to 5° C., stirred for 1 hr and filtered. The wet cake was washed with DM water (60 ml) and dried under vacuum 85 to 90° C.

Yield: 10.5 gms.
% Yield: 1.05% (w/w).
Purity: 99.78%.

The invention claimed is:

1. A cost-effective process for preparing efavirenz of formula (I) comprising reaction of a compound of formula (II) with triphosgene in an organic solvent selected from acetone, propionitrile, acetonitrile, tetrahydrofuran and 1,2-dimethoxyethane, in the presence of an inorganic base selected from sodium carbonate, potassium carbonate, sodium bicarbonate and potassium bicarbonate, neutralizing the reaction mixture, adding water and isolating compound of formula (I)

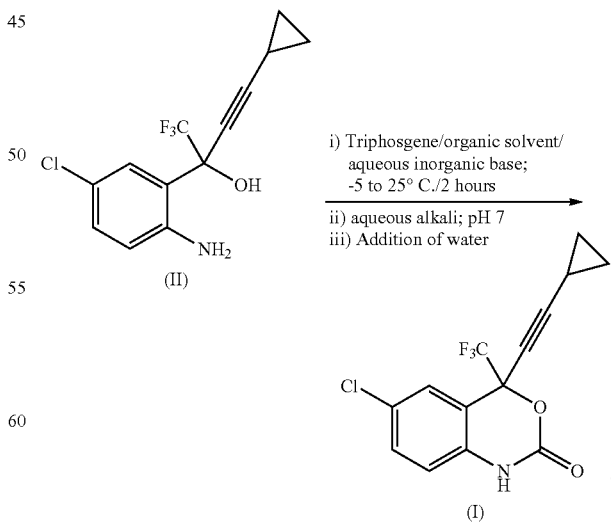

2. A process as claimed in claim 1, wherein the organic solvent is acetonitrile, acetone and 1,2-dimethoxyethane.

3. A process as claimed in claim 1 wherein the volume of solvent added is in the range of 1.0 volume to 3.0 volumes per gram of compound of formula (II).

4. A process as claimed in claim 1, wherein the inorganic base is sodium bicarbonate or potassium bicarbonate.

* * * * *